(12) United States Patent
Casella et al.

(10) Patent No.: US 6,897,218 B2
(45) Date of Patent: May 24, 2005

(54) NITRIC OXIDE DONORS BASED ON METALLIC CENTERS

(75) Inventors: Luigi Casella, Pavia (IT); Marina Ziche, Siena (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 10 days.

(21) Appl. No.: 10/399,408

(22) PCT Filed: Feb. 21, 2002

(86) PCT No.: PCT/EP02/01839

§ 371 (c)(1),
(2), (4) Date: Apr. 23, 2003

(87) PCT Pub. No.: WO02/070496

PCT Pub. Date: Sep. 12, 2002

(65) Prior Publication Data

US 2004/0029854 A1 Feb. 12, 2004

(30) Foreign Application Priority Data

Mar. 1, 2001 (IT) .................................... MI2001A0426

(51) Int. Cl.$^7$ .................... C07D 295/30; C07D 401/06; A61K 31/495; A61K 31/496; A61P 9/10
(52) U.S. Cl. ............................ 514/253.01; 514/253.12; 514/255.01; 544/360; 544/382
(58) Field of Search ....................... 514/253.01, 253.12, 514/255.01; 544/360, 382

(56) References Cited

U.S. PATENT DOCUMENTS 6,133,320 A   10/2000   Yallampalli et al. ........ 514/632

FOREIGN PATENT DOCUMENTS

| WO | 93 20088 | 10/1993 |
| WO | 96 40665 | 12/1996 |

OTHER PUBLICATIONS

David J Webb; Ian L Megson, Expert Opinion on Investigational Drugs 2002, vol. 11, No. 5, pp. 587–601.*
J.A. Hrabie et al.: "New nitric oxide–releasing zwitterions derived from polyamines" Journal of Organic Chemistry, vol. 58, No. 6, pp. 1472–1476 1993.
J.A. Hrabie et al.: "Adducts of piperazine with nitric oxide" Organic Preparations and procedures Int., vol. 31, No. 2, pp. 189–192 1999.

* cited by examiner

Primary Examiner—Thomas C. McKenzie
(74) Attorney, Agent, or Firm—Oblon, Spivak, McClelland, Maier & Neustadt, P.C.

(57) ABSTRACT

A metal complex of a piperazineNONOate derivative of the formula:

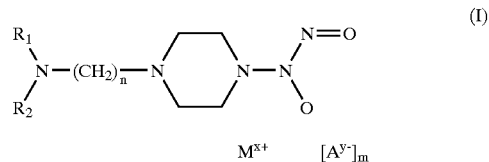

wherein a) $R_1$ and $R_2$ independently represent hydrogen, linear or branched ($C_1$–$C_4$) alkyl, optionally substituted by 1 or 2 groups selected from the group consisting of hydroxy, ($C_1$–$C_4$) alkoxy, ($C_1$–$C_4$) alkylthio, amino, ($C_1$–$C_4$) alkylamino, di-($C_1$–$C_4$) alkylamino, carboxy, carbo($C_1$–$C_4$) alkoxy, aryl, aryloxy, arylthio; or b) $R_1$ and $R_2$ taken together, represent one of the following groups =$CR_3$-aryl, where $R_3$ represents hydrogen, ($C_1$–$C_4$) linear or branched chain alkyl, optionally substituted by 1 or 2 groups selected from the group consisting of hydroxy, carboxy, aryl; n represents a whole number ranging from 2 to 4; $M^+$ represents a cation of a transition metal or zinc; x represents a whole number which varies from 1 to 3, and indicates the charge units of the cation of the transition metal or of the zinc in relation to its stable oxidation state; A – represents an inorganic or organic anion which forms stable salts with the NONOate metal complex; y represents a whole number which varies from 1 to 3, and indicates the charge of the anion; m represents a whole number including zero, or a fractional, indicating the number of anions required to balance the cationic charge of the NONOate metal complex and is related to the values of x, y, k and w by the relationship:

$$m = \frac{(x+k)-(1+w)}{y}$$

where w is the number of possible further anionic charge units and k is the number of possible further cationic charge units present in the NONOate ligand substrate. The complex of the invention exhibits an endothelio-protective effect in the coronary system and stimulates re-endothelialization and angiogenesis processes.

15 Claims, No Drawings

NITRIC OXIDE DONORS BASED ON METALLIC CENTERS

BACKGROUND OF THE INVENTION

1. Field of the Invention

The present invention relates to a class of nitric oxide (NO) releasing metal complexes characterised by the presence of a coordinated piperazineNONOate residue, and their use as pharmacological agents able to induce vascular relaxation, to exert an endothelio-protective effect on the coronary district, and to stimulate re-endothelialization and angiogenesis processes.

The invention also relates to a process for preparing the aforesaid compounds.

The invention further relates to pharmaceutical formulations containing one or more of the aforesaid compounds.

2. Description of the Background

The pharmacological activity of the compounds of the invention has been evaluated by their relaxation induction effect in vascular preparations (rabbit aorta rings) precontracted with noradrenaline (Amerini et al., J. Cardiovasc. Pharmacol., 28: 82–88, 1966). The endothelio-protective and pro-angiogenetic effects of the compounds have also been evaluated in a study on the proliferation and migration of endothelial cells of the microcirculatory system (M. Ziche et al., J. Clin. Invest. 94: 2036–2044, 1994).

Nitric oxide performs an important role in a variety of biological and physiological processes as a vasodilator, neurotransmitter and bioregulator, and is involved in the defensive immune system (Nitric Oxide: Principles and Action, J. Lancaster Jr. ed., Academic Press, San Diego, Calif. 1996). It is produced in the body enzymatically from the amino acid L-arginine by means of NO synthase (R. Iyengar, D. J. Stuehr and M. A. Marietta, Proc. Natl. Acad. Sci. USA 84, 6369, 1987), which is present in various isoforms. The action of the nitric oxide depends on its capacity to activate the enzyme guanylate cyclase and to induce in this manner the production of cyclic GMP. The constituent isoform of the NO synthase is present mainly at the endothelial level and is responsible for controlling the vasal tone. Another type of NO synthase, which is induced in activated macrophages and in other cells, synthesizes NO as a cyclotoxic agent against tumoral cells and microorganisms.

Inadequate NO production determines numerous pathological conditions, for which this molecule has to be administered from the outside. However, given that this is a radical molecule of relatively short life, it is not administered as such but via precursors. These include the classical nitrovasodilators such as nitroglycerin, sodium nitroprussiate, isoamyl nitrite and pentaerythritol tetranitrate, which have been used for some time but give rise to various problems in controlling the rate and extent of NO release and in producing side effects. The availability of molecules able to release physiologically more suitable NO concentrations with lesser side effects would therefore be of important therapeutic advantage.

SUMMARY OF THE INVENTION

The compounds of the invention are a family of metal complexes with ligands containing piperazineNONOate residues which when in solution release NO, their reference base being 4-(hydroxy-nitrosamino)-1-piperazineethaneamine, a known compound (J. A. Hrabie, J. R. Klose, D. A. Wink and L. K. Keefer, J. Org. Chem. 58, 1472, 1993), which was prepared by a procedure modified with respect to the original. The complexes derived from NONOates claimed herein allow a wide variation in the structure, the charge, the physical-chemical properties and the NO release activity. They are compounds having the following general structure:

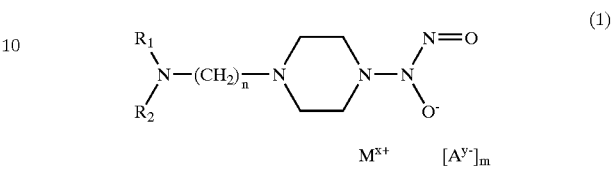

where:
a) $R_1$ and $R_2$ independently represent hydrogen, linear or branched ($C_1$–$C_4$) alkyl, possibly substituted with 1–2 groups selected from hydroxy, ($C_1$–$C_4$) alkoxy, ($C_1$–$C_4$) alkylthio, amino, ($C_1$–$C_4$) alkylamino, di-($C_1$–$C_4$) alkylamino, carboxy, carbo($C_1$–$C_4$) alkoxy, aryl, aryloxy, arylthio;

or, b) $R_1$ and $R_2$, taken together, represent one of the following groups: =$CR_3$-aryl, where $R_3$ represents hydrogen, linear or branched ($C_1$–$C_4$) alkyl, possibly substituted with 1–2 groups selected from hydroxy, carboxy, aryl;

n represents a whole number from 2 to 4 inclusive, preferably 2 or 3;

$M^+$ represents a cation of a transition metal or zinc;

x represents a whole number which can vary from 1 to 3 inclusive, and indicates the charge units of the cation of the transition metal or of the zinc in relation to its stable oxidation state;

$A^-$ represents an inorganic or organic anion which forms stable salts with the NONOate metal complex;

y represents a whole number which can vary from 1 to 3 inclusive, and indicates the charge units of the anion;

m represents a whole number including zero, or fractional, indicating the number of anions required to balance the cation charge of the NONOate metal complex and is related to the values of x, y, k and w by the relationship:

$$m = \frac{(x+k)-(1+w)}{y}$$

where w is the number of possible further anionic charge units and k is the number of possible further cationic charge units present in the NONOate ligand substrate.

DETAILED DESCRIPTION OF THE PREFERRED EMBODIMENTS

In this description and in the claims, the term "aryl" indicates a benzene or naphthalene ring possibly substituted by 1–3 groups selected from ($C_1$–$C_4$) alkyl, hydroxy, amino, ($C_1$–$C_4$) alkylamino, di-($C_1$–$C_4$) alkylamino, carboxy, carbo ($C_1$–$C_4$) alkoxy, ($C_1$–$C_4$) alkoxy, nitro, cyano, halo, phenoxy, mercapto, ($C_1$–$C_4$) alkylthio, or a heterocyclic ring with 5–6 members containing 1 or 2 heteroatoms selected from N, S, O, possibly substituted as above, and their completely or partly hydrogenated derivatives, possibly substituted with an oxo or thioxo group.

Examples of heterocyclic rings with 5–6 members containing 1 or 2 heteroatoms are: pyrrole, furan, pyrazole, imidazole, oxazole, isoxazole, thiophene, thiazole, isothiazole, pyridine, pyrazine, pyridazine, pyrimidine, pyran, 1,4-oxazine, 1,4-thiazine possibly substituted as above, and their completely or partly hydrogenated derivates possibly substituted with an oxo or thioxo group in the carbocyclic portion, and, possibly, ($C_1$–$C_4$) alkyl-substituted at the nitrogen atom, if present, such as the 1-($C_1$–$C_4$) alkyl-2(1H)pyridinones or 1-($C_1$–$C_4$) alkyl-2(1H) pyridinethiones.

The term "cation of a transition metal" identifies a cation derived from a metal selected from Ti, V, Cr, Mn, Fe, Co, Ni, Cu, Pd, Ru, Pt, Au. Examples of such cations are $Zn^{2+}$ $TiO^{2+}$, $VO^{2+}$, $Cr^{3+}$, $Mn^{2+}$, $Fe^{3+}$, $Co^{3+}$, $Ni^{2+}$, $Cu^{2+}$, $Pd^{2+}$, $Ru^{3+}$, $Pt^{2+}$, $Au^{3+}$.

The term "($C_1$–$C_4$) alkyl" and its equivalent incorporated in a radical which comprises it (e.g.: ($C_1$–$C_4$) alkoxy, ($C_1$–$C_4$) alkylamine etc.) identifies a linear or branched alkyl chain, such as methyl, ethyl, propyl, isopropyl, butyl, isobutyl, sec.butyl and tert.butyl.

The anionic charge units possibly present in the ligand substrate of the NONOate can derive from the ionization of radicals of acid type, for example carboxy, hydroxy, mercapto, possibly present as substituents in the groups represented by the radicals $R_1$ and/or $R_2$ and/or $R_3$ in the general formula (I). In this case, the aforesaid substituents also comprise the respective anionic form. In general, the value of w is a whole number between zero and 3, preferably between zero and 2, and more preferably zero or 1.

The cationic units possibly present in the ligand substrate of the NONOate can derive, for example, from the protonation of the basic portion $R_1R_2N$- in the general formula (I) and from the protonation of basic groups, e.g. amino, ($C_1$–$C_4$) alkylamino, di-($C_1$–$C_4$) alkylamino, possibly present as substituents in the groups represented by the radicals $R_1$ and/or $R_2$ and/or $R_3$. In general, the value of k is a whole number between zero and three, preferably between zero and two, and more preferably zero or 1.

The inorganic or organic cations which form stable salts with the NONOate complex can derive from the common inorganic or organic acids. Preferred are those salts with pharmaceutically acceptable acids, such as hydrochloric, hydrobromic, sulphuric, perchloric, phosphoric, acetic, propionic, ascorbic, lactic, succinic, maleic, fumaric, palmitic, cholic, mucic, camphoric, glutaric, glycolic, phthalic, tartaric, lauric, stearic, salicylic, methanesulphonic, benzenesulphonic, naphthalenesulphonic, sorbic, picric, benzoic, cinnamic, toluenesulphonic, trifluoroacetic and trifluoromethanesulphonic acid.

When the value of the sum (x+k) equals that of the sum (1+w), m assumes the value zero and hence the anion [Ay–] in the compound of formula (I) is no longer present. In fact its presence is no longer necessary as the cationic charge units present in the NONOate metal complex (x+k) are entirely compensated by the internal anionic charge units (1+w).

In general, the 1-(ω-aminoalkyl)piperazines of formula:

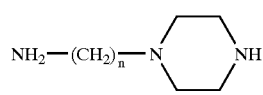

(II)

(with n=2–4) which are used as starting materials can be prepared by reacting the corresponding ω-bromoalkylphthalimides with piperazine, then hydrolyzing the phthalimido group.

4-(hydroxynitrosamino)-1-piperazineethaneamine can be prepared by reacting 1-(2-aminoethyl)piperazine with NO by the aforesaid method reported by J. A. Hrabie et al., which uses NO at a pressure of 5 atm at ambient temperature, or by the perhaps simpler and equivalently yielding method used herein in which NO is used at 1 atm, the reaction taking place in a cryostat at –25° C. The 4-(hydroxynitrosamino)-1-ω-(1-aminoalkyl)piperazine homologues of formula (III):

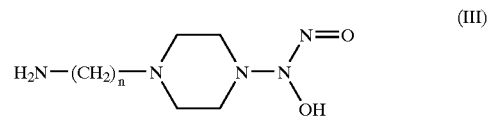

(III)

in which n represents 3 or 4, can be prepared in an analogous manner starting from the corresponding 1-(ω-aminoalkyl) piperazines and NO.

The precursors of the 4-(hydroxynitrosamino)-1-(monoor di-alkyl-ω-aminoalkyl)piperazines necessary for obtaining the metal complexes of formula (I) where $R_1$ and/or $R_2$ have meanings other than hydrogen in group a) can be obtained from the corresponding 1-(ω-aminoalkyl) piperazines, selectively protected at the secondary nitrogen atom in position 4 of the piperazino ring, by condensing a suitable carbonyl derivative, corresponding to the ($C_1$–$C_4$) alkyl group to be introduced, with the primary amino group situated in the alkyl chain (by simple heating in alcohol or under reflux in benzene with azeotropic removal of water, according to the reactivity of the carbonyl compound) followed by reduction under mild conditions (e.g. with sodium borohydride or hydrogen over Pd/C) and possible subsequent introduction, into the ω-amino group, of a second ($C_1$–$C_4$) alkyl group, possibly substituted as described in the aforesaid group a). This introduction can be effected by a corrimon alkylation process. The corresponding 4-hydroxynitrosamino derivatives are then obtained by reaction with NO under conditions analogous to the aforedescribed for the corresponding compounds in which $R_1$ and $R_2$ are both hydrogen, after eliminating the group protecting the secondary nitrogen in position 4 of the piperazino ring.

To produce the Schiff bases necessary for obtaining the complexes of general formula (I) where $R_1$ and $R_2$ taken together have the meanings of the aforesaid group b), the 4-(hydroxynitrosamino)-1-piperazineethaneamine or the 4-(hydroxynitrosamino)-1-(ω-aminoalkyl)-piperazines of formula (III) in which n represents 3 or 4, are condensed with carbonyl compounds of formula O=$CR_3$-aryl where $R_3$ has the same meanings as above.

The Schiff bases of the 4-(hydroxynitrosamino)-1-(aminoalkyl) piperazines necessary for obtaining the metal complexes of group b) are not generally isolated because their preparation requires conditions in which the piperazino residue can lose NO. The carbonyl compounds to be used for preparing the Schiff bases are either commercial products or obtainable by methods described in the literature. For example, 3-formyl-1-isopropyl2(1H)-pyridinethione and analogous derivatives containing different alkyl substituents in position 1 of the ring can be obtained by a method reported in the literature by J. Becher and E. G. Frandsen, Acta Chem. Scand., Ser. B 30, 863, 1976.

A preferred group of metal complexes of the invention consists of the compounds of formula (I) in which $R_1$ and $R_2$ both represent hydrogen or, taken together, represent a =$CR_3$-aryl group where $R_3$ is hydrogen, the term "aryl" identifying a benzene or pyridine ring, possibly substituted by a hydroxy or mercapto group, preferably in ionized anionic form, or partly hydrogenated and possibly substituted by a ($C_1$–$C_4$) alkyl group at the nitrogen atom and by an oxo or a thioxo group in the carbocyclic portion; and n represents the number 2 or 3, preferably the number 2.

Examples of metal complexes prepared in accordance with the invention are the following:

the complex of copper(II) with the anion of 4-(hydroxynitrosamino)-1-piperazineethaneamine with perchlorate as counter-ion,

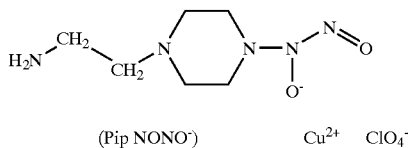

(Pip NONO⁻)   $Cu^{2+}$   $ClO_4^-$ identified as [Cu(PipNONO)][$ClO_4$] and corresponding to the general formula (I) where:

$R_1=R_2$=hydrogen; $M^{x+}=Cu^{2+}$; $A^{y-}=ClO_4-$; (x+k)=2, (1+w)=1; y=1; m=1.

the complex of nickel(II) with the dianion of the Schiff base formed from salicylaldehyde and 4-(hydroxynitrosamino)-1-piperineethaneamine:

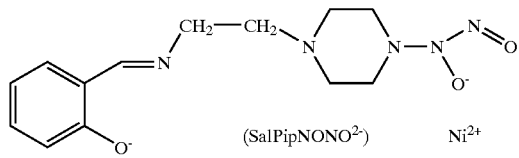

(SalPipNONO²⁻)   $Ni^{2+}$ identified as [Ni(SalPipNONO)] and corresponding to the general formula (I) where:

$R_1+R_2$=[=CH—(2-(⁻O)C6H4)]; $M^{x+}=Ni^{2+}$; (x+k)=2, (1=w)=2; m=0.

the complex of copper (II) with the anion of the Schiff base derived from condensing 3-formyl-1-isopropyl-2(1H)-pyridinethione with 4-(hydroxynitrosamino)-1-piperazineethaneamine:

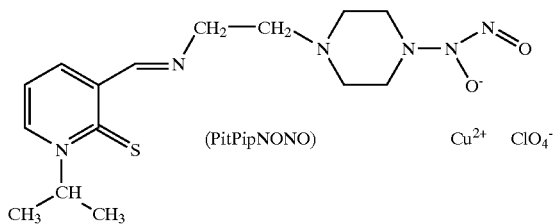

(PitPipNONO)   $Cu^{2+}$   $ClO_4^-$ with perchlorate as counter-ion, identified as [Cu(PitPipNONO)][$ClO_4$] and corresponding to general formula (I) where:

$R_1+R_2$=[=CH-(1-(2-propyl)-2(1H)-thioxo-3-pyridyl)]; $M^{x+}=Cu^{2-}$; $Ay^-=ClO_4-$; (x+k)=2, (1+w)=1; y=1; m=1.

the complex of nickel(II) with the anion of the Schiff base derived from condensing 2-formylpyridine with 4-(hydroxynitrosamino)-1-piperazineethaneamine:

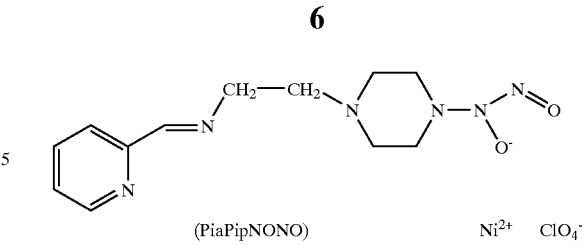

(PiaPipNONO)   $Ni^{2+}$   $ClO_4^-$ with perchlorate as counter-ion, identified as [Ni(PiaPipNONO)][$CLO_4$] and corresponding to the general formula (I) where:

$R_1+R_2$=[=CH-(2-pyridyl)]; $M^{x+}=Ni^{2+}$; $A^{y-}=ClO_4-$; (x+k)=2,(1+w)=1;y=1;m =1.

The process for preparing the metal complexes derived from 4-(hydroxynitrosamino)-(aminoalkyl)-piperazines or their Schiff bases, according to the present invention, is based on the following general methods and reactions.

The complexes of 4-(hydroxynitrosamino)-1-(ω-aminoalkyl)-piperazines with metal ions pertaining to group a) of formula (I) are prepared by reacting stoichiometric quantities of a ligand of formula (IV)

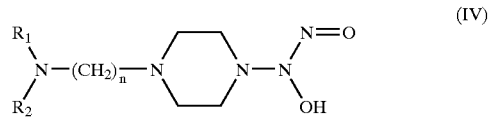

(IV)

where $R_1$ and $R_2$ have the same meanings as in formula (I), group a), and n represents a whole number from 2 to 4 inclusive, preferably 2 or 3, with a salt of a transition metal or zinc in an inert organic solvent in the presence of an equivalent quantity of alkaline base. The inert organic solvents generally used are the lower alkanols of 1–4 carbon atoms, preferably ethanol and methanol. The transition metals or zinc used are preferably those with the same anion [$A^{y-}$] which salifies the complex of formula (I) to be obtained. A complex of formula (I) in which [$A^{y-}$] represents a certain anion can, in any event, be transformed into another complex of formula (I) in which [$A^{y-}$] represents a different anion by simple ion exchange reactions. The resultant complexes are generally very soluble in the lower alkanols, in particular in methanol, and to isolate them it may be necessary to add diethyl ether to the reaction solution, preferably under cold conditions. The products are isolated by filtration or centrifugation and purified by washing with small quantities of cold methanol-diethyl ether mixtures or simply with diethyl ether. The said procedure is also applicable for obtaining complexes of formula (I) of group b) in which $R_1$ and $R_2$ taken together represent a =CR3-aryl group where $R_3$ has the above meaning. In that case the ligand used is represented by the product of formula (IV) in which $R_1$ and $R_2$ have the same meanings as in formula (I), group b), and n represents a whole number from 2 to 4 inclusive, preferably 2 or 3. The said ligand can be prepared by condensing 4-(hydroxynitrosamino)-1-(ω-aminoalkyl)-piperazine of the above formula (III), where n represents a whole number from 2 to 4 inclusive, preferably 2 or 3, with a carbonyl compound of formula O=$CR_3$-aryl where $R_3$ has the same meanings as in formula (I), group b).

Condensation of the carbonyl compound with the 4-(hydroxynitrosamino)-1-(ω-aminoalkyl)-piperazine of formula (III) is considerably accelerated if metal ions are present, by the well known template effect, to the extent that the complexes of these imino derivatives can be conveniently obtained under mild conditions by treating the carbonyl compound, the 4-(hydroxynitrosamino)-1-(ω-aminoalkyl)-piperazine and the salt of the transition metal or zinc, in the presence of an equivalent quantity of alkaline base, in an inert organic solvent, preferably ethanol or methanol, at ambient temperature or at lower temperatures. The complexes generally at least partly precipitate under these conditions; adding ethyl ether can complete the precipitation. The precipitates are filtered off or centrifuged and washed with small quantities of cold methanol-ethyl ether mixtures or only with ethyl ether, depending on their solubility.

The metal complexes have been characterised by elemental analysis (C, H, N) and by IR, UV-Vis spectroscopy and NMR (for diamagnetic complexes).

The following examples illustrate the invention but without limiting it.

EXAMPLE 1

Synthesis of the Complex [Cu(PipNONO)][ClO$_4$].

50 mg of 4-(hydroxynitrosamino)-1-piperazineethaneamine (0.26 mmoles) are dissolved in 5 ml of a methanolic solution containing an equimolar quantity of NaOH. An equivalent quantity of Cu(ClO$_4$)$_2$.6H$_2$O dissolved in a few ml of methanol is added to this solution. While maintaining the solution cold under agitation a blue-violet product is seen to precipitate and is separated by centrifugation and washed many times with small quantities of cold ether. The product is then dried under vacuum (yield 33%). Analytical data confirm its composition.

EXAMPLE 2

Synthesis of the Complex [Ni(SalPipNONO)].

50 mg of 4-(hydroxynitrosamino)-1-piperazineethaneamine (0.26 mmoles) are dissolved in 5 ml of a methanolic solution containing an equimolar quantity of NaOH. 27.6 μl of salicylic aldehyde (0.26 mmoles) are added to the solution by means of a micropipette to obtain an immediate yellow coloration, followed by 34.2 mg of cold NiCl$_2$ under agitation. The complex with the Schiff base, of yellow-green colour, is precipitated by adding cold diethyl ether. It is then centrifuged, washed with small quantities of cold diethyl ether and dried under vacuum (yield 43%). Analytical data confirm its composition.

The pharmacological test for characterising the activity of NO release from the compounds is the relaxation of a rabbit aorta precontracted with noradrenaline (Amerini et al., J. Cardiovasc. Pharmacol., 28: 82–88, 1996). The vascular preparations precontracted with the ED$_{50}$ dose of noradrenaline are treated with increasing doses of the complexes under study (1 nM–100 μM). The vasorelaxation effect is compared with that of classical NO donors such as sodium nitroprussiate and spermineNONOate.

The complexes derived from 4-(hydroxynitrosamino)-1-(aminoalkyl)-piperazines according to the present invention are all able to induce powerful vascular relaxation. For example, the order of magnitude of the power of [Ni(SalPipNONO)], [Cu(PipNONO)][ClO$_4$], [Cu(SalPipNONO)], compared with sodium nitroprussiate, varies in accordance with the following ED$_{50}$ values: [Ni(SalPipNONO)] 30 nM, [Cu(PipNONO)][ClO$_4$] 100 nM, [Cu(SalPipNONO)] and sodium nitroprussiate3 μM. SpermineNONOate is much less powerful than piperazineNONOate complexes. The kinetics of insurgence and duration of the biological effect of the complexes can be superimposed on that obtained with sodium nitroprussiate.

Control tests to demonstrate that the aorta relaxation effect is specific and associated with the release of NO were carried out by studying an analogue of the complex [Ni(SalPipNONO)] lacking the NONOate residue bound to the piperazine nucleus; it was found to be totally inactive. Moreover, the presence of ODQ {1H-[1,2,4]oxadiazolo[4,3-a]quinoxalin-1-one}, a selective inhibitor of guanylate cyclase, completely eliminates the relaxation effect of [Ni(SalPipNONO)].

The endothelio-protective and pro-angiogenetic effect of the compounds was also evaluated by measuring the growth promotion and migration effect on endothelial cells of the microcirculatory system compared with other NO donors. Cell migration was evaluated using Boyden chambers, and proliferation as the total number of cells after 48 hours of exposure to the substances under study (M. Ziche et al., J. Clin. Invest. 94: 2036–2044, 1994).

The complexes derived from the 4-(hydroxynitrosamino)-1-(ω-aminoalkyl)-piperazines according to the present invention are able to induce endothelial cell proliferation and migration. The effect on migration is dose-dependent (1 nM–1 μM) with maximum activity at 100 nM and 1 μM. The complexes are likewise active and are more powerful than sodium nitroprussiate, which shows maximum activity at 100 μM concentration, whereas spermineNONOate is little active and does not give the maximum effect observed with the other NO donors. The effect on proliferation was tested at increasing compound concentrations (1 nM–1 μM). An increase in cell proliferation is observed at doses of 10 and 100 nM, with greater effect at the lower dose. At 1 μM the number of cells is equal to that of the control. The most active complex is again [Ni(SalPipNONO)]. Those analogues of the compounds lacking the NONOate residue bound to the piperazine nucleus were found to be completely inactive. Again, in the presence of ODQ, the selective inhibitor of guanylate cyclase, proliferation promotion by the complexes is completely eliminated.

Compounds with NO release activity are used in many therapeutic fields as demonstrated by ample references in the scientific and/or patent literature, some of which are cited below by way of example:

U.S. Pat. No. 6,103,275
U.S. Pat. No. 6,133,320
Bauer J A
Hydroxocobalamins as biologically compatible donors of nitric oxide implicated in acceleration of wound healing.
Med Hypotheses, 1998 July; 51(1): 65–7
Dusting G J, Fennessy P., Yin Z L, Gurevich V,
Nitric oxide in atherosclerosis: vascular protector or villain?
Clin Exp Pharmacol Physiol Supp. Nov. 25, 1998; S34–41.
Weis M, Meiser B M, Reichart B, von Scheidt W
The continuing challenge of cardiac transplant arteriosclerosis.
Cardiologia, 1998 August; 43(8); 777–87
Smith G N, Brein J F
Use of nitroglycerin for uterine relaxation
Obstet Gynecol Surv. 1998 Sep; 53(9); 559–65
McCurry K r, Keenan R J.
Controlling perioperative morbidity and mortality after lung transplantation for pulmonary hypertension
Semin Thorac Cardiovasc Surg. 1998 April; 10(2): 139–43
Thomsen L L, Olesen J
Nitric oxide theory of migraine
Clin Neurosci, 1998; 5(1): 28–33
Motwani J G, Topol E J Aortocoronary saphenous vein graft disease: pathogenesis, predisposition, and prevention
Circulation, Mar. 10, 1998; 97(9): 916–31
Bzeizi K J, Jalan R, Plevris J N, Hayes P C
Primary graft dysfunction after liver transplantation: from pathogenesis to prevent
Liver Transpl Surg. 1997 March; 3(2): 137–48
Melis M R, Argiolas A
Role of central nitric oxide in the control of penile erection and yawning.
Prog Neuropsychopharmacol Biol Psychiatry, 1997 August; 21(6): 899–922
Schultheiss D, Stief C G, Truss M C, Jonas U
Pharmacological therapy in erectile dysfunction-current standards and new view
Wien Med Wochenschr, 1997; 147(4–5): 102–4
Lefer A M, Lefer D J
The role of nitric oxide and cell adhesion molecules on the microcirculation in ischaemia-reperfusion
Cardiovasc Res. 1996 October; 32(4): 743–51
Ku DD
Nitric oxide—and nitric oxide donor—induced relaxation
Methods Enzmol. 1996; 269:107–19
Ziche M, Morbidelli L, Masini E, Amerini S, Granger H J, Maggi C A, Geppetti P, Ledda F, Nitric oxide mediates angiogenesis in vivo and endothelial cell growth and migration in vitro promoted by substance P. J Clin Invest 1994; 94(5): 2036–44.
Ziche M, Morbidelli L, Masini E, Granger H, Geppetti P, Ledda F, Nitric oxide promotes DNA synthesis and cyclic GMP formation in endothelial cells from postcapillary venules.
Biochem Biophys Res Commun. 1993; 192(3): 1198–203.

The compounds according to this invention can therefore be used for the therapy of illnesses and/or dysfunctions relating to:
a) the cardiovascular system, such as: hypertension, angina, atherosclerosis, ischemia of the myocardium, etc.
b) the female reproductive system such as: infertility, dysmenorrhea, premature birth, endocrine dysfunctions, osteoporosis etc.
c) the male reproductive system, such as: impotence, male menopause syndromes, endocrine dysfunctions, prostatic hypertrophy, etc.
d) the central nervous system, such as: neurological and behavioural disturbances, epilepsy, Alzheimer's disease, etc.
e) inflammatory processes, such as: autoimmune and immune illnesses, acute inflammation, arthritis, transplant rejection.
f) internal organ functions, such as: kidney (e.g. hypertension, stenosis of the renal artery), pancreas (e.g. diabetis) and bladder (e.g. incontinence).
g) the cutaneous system, such as eczema, acne, wounds and burns.
h) growth and diffusion of tumours.

The compounds of the invention can be used as such or can be formulated in combination with other medicaments (e.g. non-steroidal anti-inflammatory, Del Soldato et al., TiPS, 20: 319–323, 1999).

The doses can vary according to age, the method of administration and the state of the patient in relation to the illness. In general the effective dosages vary within orders of magnitude from 0.015 μg/kg to 1.50 mg/kg of the patient's weight, in relation to the state thereof, the illness and the method of administration.

The compounds of the invention can be administered by sublingual, transmucous, inhalatory, oral, intramuscular, intravenous, transdermic or topical administration.

The pharmaceutical dosage forms vary according to the type of administration and are generally prepared by the known methods of the art.

What is claimed is:

1. A metal complex of a piperazineNONOate derivative of formula:

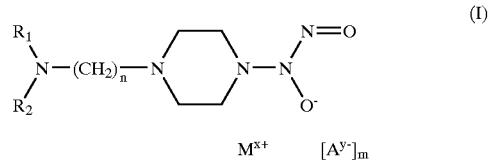

where
a) $R_1$ and $R_2$ independently represent:
hydrogen, linear or branched ($C_1$–$C_4$) alkyl, optionally substituted by 1 or 2 groups selected from the group consisting of hydroxy, ($C_1$–$C_4$) alkoxy, ($C_1$–$C_4$) alkylthio, amino, ($C_1$–$C_4$) alkylamino, di-($C_1$–$C_4$) alkylamino, carboxy, carbo($C_1$–$C_4$) alkoxy, aryl, aryloxy, arylthio; or
b) $R_1$ and $R_2$ taken together, represent one of the following groups:
=$CR_3$-aryl, where $R_3$ represents hydrogen, ($C_1$–$C_4$) linear or branched chain alkyl, optionally substituted by 1 or 2 groups selected from the group consisting of hydroxy, carboxy, aryl; n represents a whole number ranging from 2 to 4; $M^+$ represents a cation of a transition metal or zinc; x represents a whole number which varies from 1 to 3, and indicates the charge units of the cation of the transition metal or of the zinc in relation to its stable oxidation state; $A^{31}$ represents an inorganic or organic anion which forms stable salts with the NONOate metal complex; y represents a whole number which varies from 1 to 3, and indicates the charge of the anion; m represents a whole number including zero, or a fractional value, indicating the number of anions required to balance the cationic charge of the NONOate metal complex and is related to the values of x, y, k and w by the relationship:

$$m = \frac{(x+k)-(1+w)}{y}$$

where w is the number of possible further anionic charge units and k is the number of possible further cationic charge units present in the NONOate ligand substrate.

2. The metal complex of claim 1, wherein the cation is selected from the group consisting of $Zn^{2+}$, $TiO^{2+}$, $VO^{2+}$, $Cr^{3+}$, $Mn^{2+}$, $Fe^{3+}$, $Co^{3+}$, $Ni^{2+}$, $Cu^{2+}$, $Pd^{2+}$, $Ru^{3+}$, $Pt^{2+}$ and $Au^{3+}$.

3. The metal complex of claim 1 or 2, wherein the value of m is zero or, if the value of m is other than zero, the anion is an anion derived from an acid selected from the group consisting of hydrochloric, hydrobromic, sulphuric, perchloric, phosphoric, acetic, propionic, ascorbic, lactic, succinic, maleic, fumaric, palmitic, cholic, mucic, camphoric, glutaric, glycolic, phthalic, tartaric, lauric, stearic, salicylic, methanesulphonic, benzenesulphonic, naphthalenesulphonic, sorbic, picric, benzoic, cinnamic, toluenesulphonic, trifluoracetic and trifluoromethanesulphonic acid.

4. The metal complex of claim 1, wherein $R_1$ and $R_2$ both represent hydrogen or, taken together, represent a =$CR_3$-aryl group where $R_3$ is hydrogen and aryl is a benzene or pyridine ring, optionally substituted by a hydroxyl or mercapto group or a partly hydrogenated pyridine ring optionally substituted by a ($C_1$–$C_4$) alkyl group at the nitrogen atom and by an oxo or a thioxo group in the carbocyclic portion; and n represents the number 2 or 3.

5. The metal complex of claim 4, wherein $R_1$ and $R_2$ both represent hydrogen or, taken together, represent the radical:

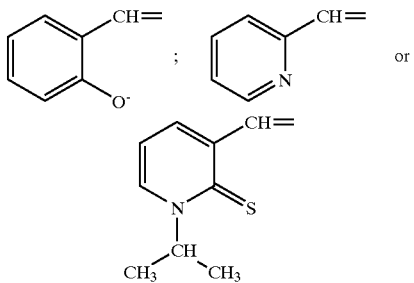

the cation $M^{x+}$ being selected from the group consisting of $Cu^{2+}$ and $Ni^{2+}$.

6. The metal complex of claim 5 which is selected from the group consisting of compounds of the formulas:

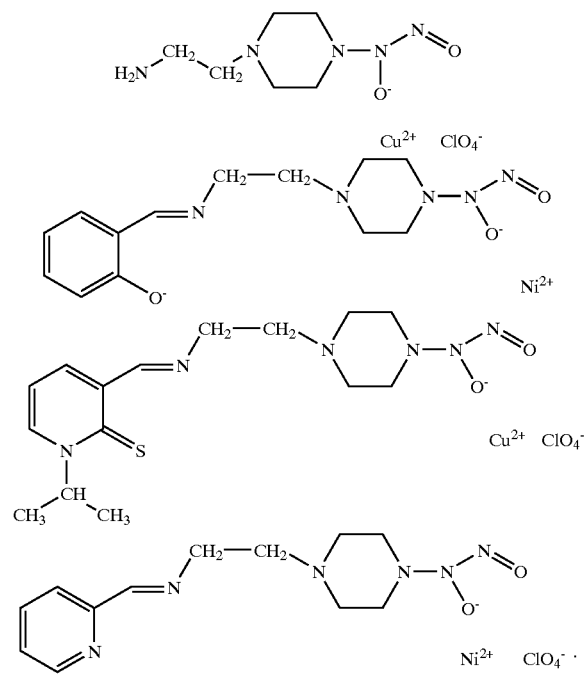

7. The metal complex of claim 4, wherein the aryl of the =$CR_3$-aryl group is a benzene or pyridine ring that is substituted by a hydroxyl or mercapto group in ionized anionic form, and wherein n is 2.

8. The metal complex of claim 1, wherein n is 2 or 3.

9. The metal complex of claim 1, wherein, aryl in said =$CR_3$-aryl group, is a 5- or 6-membered heterocyclic ring system containing 1or 2 heteroatoms selected from the group consisting of N, S and O.

10. The metal complex of claim 9, wherein said 5- or 6-membered heterocyclic ring system is pyrrole, furan, pyrazole, imidazole, oxazole, isoxazole, thiophene, thiazole, isothiazole, pyridine, pyrazine, pyridazine, pyrimidine, pyran, 1,4-oxazine or 1,4-thiazine.

11. A medicament, comprising:
   a therapeutically effective amount of a piperazineNONOate derivative of formula (I) as defined in claim 1 and a pharmaceutically acceptable carrier.

12. A method, comprising:
   treating a subject suffering from angina with the medicament of claim 11.

13. A process for preparing a metal complex of the piperazineNONOate of formula (I) of claim 1, consisting of reacting stoichiometric quantities of a ligand of the formula:

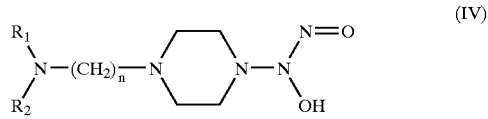

in which n, $R_1$ and $R_2$ have the same meanings as defined in formula (I), with a salt of a transition metal or zinc in an inert organic solvent in the presence of an equivalent quantity of an alkaline base.

14. The process as claimed in claim 13, wherein said piperazineNONOate of formula (I) is prepared by reacting stoichiometric quantities of said ligand of formula (IV), which is the 4-(hydroxynitrosamino)-1-(ω-aminoalkyl) piperazine of formula (III):

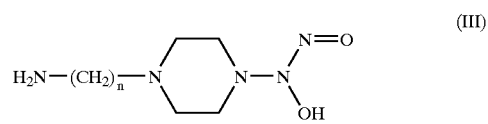

in which n is an integer of 2 to 4, with a carbonyl compound of formula O=$CR_3$-aryl, where $R_3$ is as defined, and a salt of a transition metal or zinc in an inert organic solvent in the presence of an equivalent quantity of an alkaline base.

15. The process as claimed in claim 13, or 14, wherein the inert organic solvent is ethanol or methanol and the reaction is conducted at ambient temperature or at lower temperature.

* * * * *